(12) United States Patent
Wang et al.

(10) Patent No.: US 6,856,824 B1
(45) Date of Patent: Feb. 15, 2005

(54) APPARATUS AND METHOD FOR DETECTING ABNORMALITIES IN BODILY MATTER

(75) Inventors: Wei Wang, Oadby (GB); Malcolm McCormick, Sheffield (GB)

(73) Assignee: De Montfort University, Leicester (GB)

( * ) Notice: Subject to any disclaimer, the term of this patent is extended or adjusted under 35 U.S.C. 154(b) by 0 days.

(21) Appl. No.: 09/763,908

(22) PCT Filed: Oct. 1, 1998

(86) PCT No.: PCT/GB98/02952

§ 371 (c)(1),
(2), (4) Date: May 17, 2001

(87) PCT Pub. No.: WO00/12005

PCT Pub. Date: Mar. 9, 2000

(30) Foreign Application Priority Data

Aug. 28, 1998 (GB) .............................................. 9818790

(51) Int. Cl.[7] .............................. A61B 5/05; A61B 6/00
(52) U.S. Cl. ......................................... 600/425; 378/21
(58) Field of Search ................................. 600/425, 407, 600/426, 427, 428, 429, 413, 410, 411, 412; 378/21, 1, 4, 5, 6, 7; 601/107; 324/307, 308, 309

(56) References Cited

U.S. PATENT DOCUMENTS

| 5,704,355 | A | | 1/1998 | Bridges | |
|---|---|---|---|---|---|
| 6,494,832 | B1 | * | 12/2002 | Feldman et al. | 600/301 |
| 6,535,754 | B2 | * | 3/2003 | Fishbein et al. | 600/422 |
| 6,681,132 | B1 | * | 1/2004 | Katz et al. | 600/410 |

OTHER PUBLICATIONS

"Breast Cancer Detection Using Electrical Impedance Tomography: Spice Simulation," Kejariwal et al., Published Oct. 28, 1993.

"Multi–Frequency Static Imaging in Electrical Impedance Tomography: Part 1 Instrumentation Requirements," Riu et al., *2200 Medical & Biological Engineering & Computing 33* Nov., (1995) No. 6, Stevenage, Herts., GB.

"Dielectric Properties of Breast Carcinoma and the Surrounding Tissues," Surowiec et al. *,IEEE Transactions on Biomedical Engineering*, vol. 35, No. 4, Apr. 1988.

"Baseline Electrical Impedance Measurements at Various Skin Sites—Related to Age and Sex," Nicander et al., *Skin Research and Technology* 1997, 3: 252–258, Printed in Denmark.

"Using Electrical Impedance Tommography (sic)to Identify Cancer," Cheng et al., *Chinese Journal of Biomedical Engineering (English Edition)* V. 6 No. 3, 1997.

"Electropotential Measurements as a New Diagnostic Modality for Breast Cancer," Cuzick et al., *The Lancet* vol. 352, Aug. 1, 1998.

(List continued on next page.)

*Primary Examiner*—Daniel Robinson
(74) *Attorney, Agent, or Firm*—Wallenstein Wagner & Rockey, Ltd.

(57) ABSTRACT

There is disclosed electrical impedance tomography apparatus adapted to detect abnormalities in bodily matter comprising: electrical signal generating means for generating electrical signals at a plurality of frequencies; an electrode arrangement for applying the electrical signals to the bodily matter and detecting electrical impedance properties of the bodily matter; and data processing means for correlating the detected electrical impedance properties with the presence or absence of abnormalities in the bodily matter; in which electrical signals of a frequency greater than 1 MHz, preferably greater than 2 MHz, more preferably greater than 3 MHz and most preferably greater than 4 MHz are applied to the bodily matter.

18 Claims, 3 Drawing Sheets

OTHER PUBLICATIONS

Figure 1:
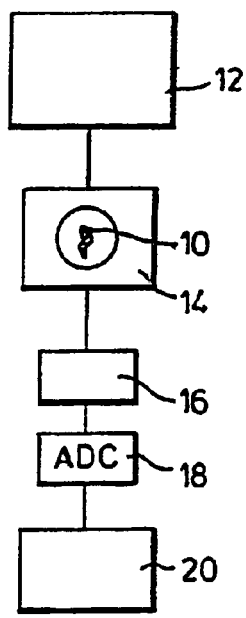

"Review—*Clinical Applications of Electrical Impedance Tomography*," Dijkstra et al., *Journal of Medical Engineering & Technical*, vol. 17, No. 3 (May/Jun. 1993), pp. 89–98.

"*Variability of Impedivity in Normal and Pathological Breast Tissue*," Jossinet, *Medical & Biological Engineering & Computing*, Sep. 1996.

* cited by examiner

APPARATUS AND METHOD FOR DETECTING ABNORMALITIES IN BODILY MATTER

This invention relates to an apparatus and method for detecting abnormalities in bodily matter, with particular, but by no means exclusive, reference to the detection of breast carcinomas.

Breast cancer is a major cause of mortality in Western countries. In the UK, one in twelve women develop this condition during their lifetime.

Conventionally, screening for breast cancer has employed x-ray mammography. The x-ray images produced thereby are analysed by eye to determine whether any abnormalities are present. Should a potential abnormality be located, further analysis by surgery typically a tissue biopsy, is usually required. Clearly, a non-invasive alternative procedure for investigating breast lesions would be highly desirable. Other disadvantages with x-ray mammography are that ionising radiation is employed, and that identification of lesions from the x-ray image requires a background comprising a substantially contrasting material. As a result, the ability of x-ray mammography to identify low radio-density tumours, and tumours in younger woman, is limited. A further and highly significant disadvantage is that a tumour must be relatively large (for example at least 5 millimetres) before detection is possible with X-ray mammography.

Electrical impedance tomography (EIT) is a well known technique which provides 2 dimensional images or "slices" through an object using an array of electrodes which typically encircle the object. The images are obtained by applying current to the object via selected electrodes, and detecting the potentials generated at other electrodes in the array. The measured potentials depend on the electrical impedance of the object and from these data it is possible to perform a back projection technique to construct an image of the electrical impedance of the objects. By performing a plurality of such measurements, both 2- and 3-dimensional image can be assembled.

Dijkstra et al (A. K. Dijkstra B. H. Brown, A. D. Leathlard, N. D. Harris, D. C. Barber and D. L. Edbrooke; Journal of Medical Engineering & Technology, 17 (1993) 89–98) provides an overview of clinical applications of EIT. Images may be static or dynamic, i.e., representing changes in impedance of the subject over a period of time, an example being an image of the thorax during breathing. It is noted in Dijkstra et al that EIT produces images of body function and not high quality anatomical images. Elsewhere in Dijksta et al it is commented that static images are technically difficult to produce and that there is no clinical experience with static EIT images. Thus, the teaching of Dijkstra et al is towards the production of dynamic images of body function, and away from the analysis of specific abnormalities, such as carcinomas, via static EIT.

The present invention is concerned with an improved EIT technique which enables non-invasive detection and imaging of abnormalities in bodily matter, a primary, but non-limiting, example of which is the detection and imaging of breast carcinomas.

According to a first aspect of the invention there is provided electrical impedance tomography apparatus adapted to detect abnormalities in bodily mater comprising:

electrical signal generating means for generating electrical signals at a plurality of frequencies;

an electrode arrangement for applying the electrical signals to the bodily matter and detecting electrical impedance properties of the bodily matter; and data processing means for correlating the detected electrical impedance properties with the presence or absence of abnormalities in bodily matter;

in which electrical signals of a frequency greater than 1 MHz, preferably greater than 2 MHz, more preferably greater than 3 MHz and most preferably greater than 4 MHz for example 5 MHz, are applied to the bodily mater.

At such high applied frequencies, differences between normal tissue and abnormal tissue are more pronounced, permitting the detection of abnormalities by EIT.

The apparatus may be adapted to detect a carcinoma, which may be a breast carcinoma. In contrast to x-ray mammography, ionising radiation is not employed, and the technique may be successfully applied to younger women and/or to tumours of low radio-density. Furthermore, it is possible to provide a 3 dimensional image, possibly leading to more accurate determination of the position of a carcinoma.

The apparatus may be adapted to detect a stage 3 carconoma and/or a stage 2 carcinoma and/or a stage 1 carcinoma. These stages are defined in Tables 1 and 2, below.

The data processing means may correlate the detected electrical impedance properties with the presence or absence of abnormalities using a fractal model of tissue impedance.

Information related to dispersion frequencies may be used to perform the correlation.

The ratio of extra-cellular impedance and intra-cellular impedance may be used to perform the correlation. The ratio of extra-cellular impedance and "membrane" impedance may be used to perform the correlation.

The data processing means may reference the detected electrical impedance properties of the bodily matter to the detected electrical impedance properties of other bodily matter. In the case of breast carcinoma detection, the impedance properties may be referenced to detected electrical impedance properties of fat tissue or ductal/stroma tissue in the breast.

The data processing means may be adapted to compare the detected electrical impedance properties with a database of impedance properties corresponding to bodily matter of known composition. The database may comprise impedance properties of bodily mater obtained from subjects of differing and known ages, heights, weights or races, or normalised figure.

At least the electrode arrangement may be disposed in a women's brassiere. The permits screening without the physical discomfort associated with x-ray mammography.

According to a second aspect of the invention there is provided an electrical impedance tomographic method for detecting abnormalities in bodily matter comprising the steps of:

generating electrical signals at a plurality of frequencies;

applying said electrical signals to the bodily matter;

detecting electrical impedance properties of the bodily matte; and correlating the detected impedance properties with the presence or absence of abnormalities in the bodily matter;

in which electrical signals of a frequency greater than 1 MHz, preferably greater than 2 MHz, more preferably greater then 3 MHz and most preferably greater than 4 MHz are applied to the bodily matter.

The abnormality may be a carcinoma, which may be a breast carcinoma.

A stage 3 carcinoma and/or a stage 2 carcinoma and/or and stage 1 carcinoma may be detected.

The correlation of the detected impedance properties with the presence or absence of abnormalities may use a ideal model of tissue impedance.

Information related to dispersion frequencies may be used to perform the correlation.

The ratio of intra-cellular impedance and extra-cellular impedance may be used to perform the correlation. Other ratio smay be used in addition to the extra-cellular vs. intra-cellular impedance. These may include for exmple the intra-cellular impedance divided by the cellular capacitance, which may provide a significant index indicating the abnormality of the tissue. Other ratios which may be used are given in Tables 3–5 (below).

The detection of impedance properties of the bodily matter may be performed at a controlled temperature. The detected electrical impedance properties of the bodily matter may be referenced to detected electrical impedance properties of other body matter. In the case of breast carcinoma detection the impedance properties may be referenced to detected electrical impedance properties of other tissues within the breast, for example a normalised response of stroma.

The detected electrical impedance properties may be compared with a database of impedance properties corresponding to bodily matter of known composition. The database may comprise impedance properties of bodily matter obtained from subjects of differing and known ages. The temperature at which readings were obtained and the post-excision age of the bodily matter of the database may also be used in any comparison.

TABLE 1

TNM classification and staging for breast cancer

| Classification | Primary tumour (T) |
| --- | --- |
| TX | Primary tumour cannot be assessed |
| T0 | No evidence of primary tumour |
| Tis | Carcinoma in situ (ductal or lobular or Paget's disease with no tumour) |
| T1 | Tumour 2 cm or less in greatest dimension |
| T1a | 0.5 cm or less in greatest dimension |
| T1b | More than 0.5 cm but not more than 1 cm in greatest dimension |
| T1c | More than 1 cm but not more than 2 cm in greatest dimension |
| T2 | Tumour more than 2 cm but not more than 5 cm in greatest dimension |
| T3 | Tumour more than 5 cm in greatest dimension |
| T4 | Tumour of any size with direct extension to chest wall or skin |
| T4a | Extension to chest wall |
| T4b | Edema (including peau d'orange) or ulceration of skin breast or satellite skin nodules confined to same breast |
| T4c | Both (T4a and T4b) |
| T4d | Inflammatory carcinoma |
| | Regional lymph nodes (pathologic pN) |
| pNX | Regional nodes cannot be assessed |
| pN0 | No regional node metastases |
| pN1 | Metastases to movable ipsilateral axillary nodes |
| pN1a | Micrometastases only (none larger than 0.2 cm) |
| pN1b | Metastasis to node(s), any larger than 0.2 cm |
| pN1bi | Metastasis in 1 to 3 nodes, any more than 0.2 cm and all less than 2 cm in greatest dimension |
| pNbii | Metastasis to 4 or more nodes, any more than 0.2 cm and all less than 2 cm in greatest dimension |
| pNbiii | Extension of tumour beyond node capsule; metastasis less than 2 cm in greatest dimension |
| pNbiv | Metastasis greater than 2 cm in greatest dimension to a node |

TABLE 1-continued

TNM classification and staging for breast cancer

| Classification | Primary tumour (T) |
| --- | --- |
| pN2 | Metastasis to ipsilateral axillary nodes that are fixed to one another or to other structures |
| pN3 | Metastasis to ipsilateral internal mammary nodes |
| | Distant metastasis (M) |
| MX | Presence of distant metastasis cannot be assessed |
| M0 | No distant metastases |
| M1 | Distant metastasis (includes metastasis to ipsilateral supraclavicular nodes) |

TABLE 2

Stage Group for Breast Cancer

| Stage 0 | Tis | N0 | M0 |
| --- | --- | --- | --- |
| Stage 1 | T1 | N0 | M0 |
| Stage IIA | T0 | N1 | M0 |
| | T1 | N1 | M0 |
| | T2 | N0 | M0 |
| Stage IIB | T2 | N1 | M0 |
| | T3 | N0 | M0 |
| Stage IIIA | T0 | N2 | M0 |
| | T1 | N2 | M0 |
| | T2 | N2 | M0 |
| | T3 | N1 | M0 |
| | T3 | N2 | M0 |
| Stage IIIB | T4 | Any N | M0 |
| | Any T | N3 | M0 |
| Stage IV | Any T | Any N | M1 |

(Source: American Joint Committee on Cancer (AJCC) and International Union Against Cancer (UICC)1992)

Figure 2:
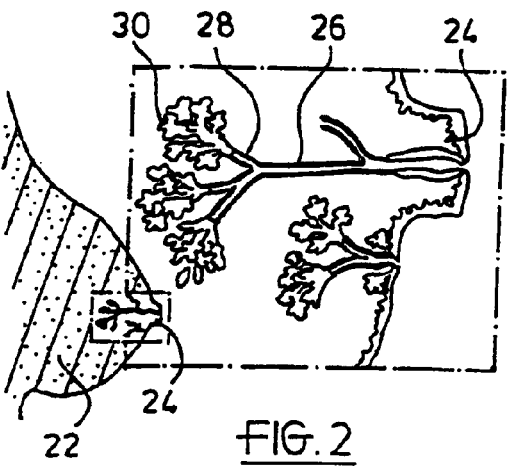
Figure 5:
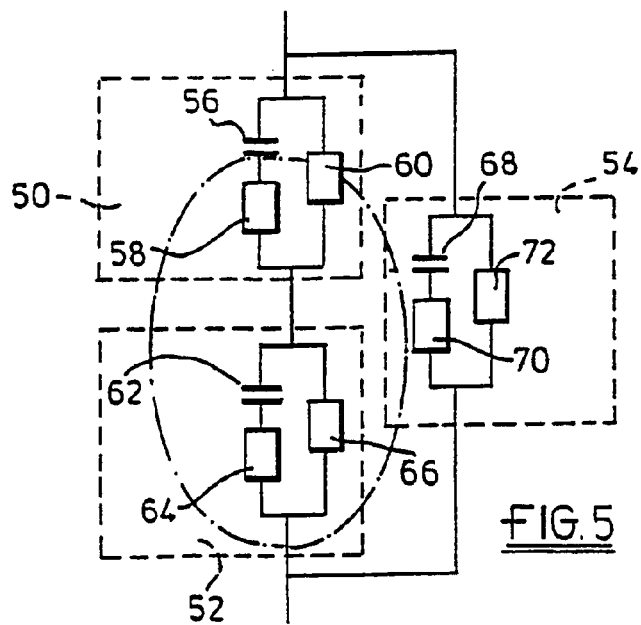
Figure 3:
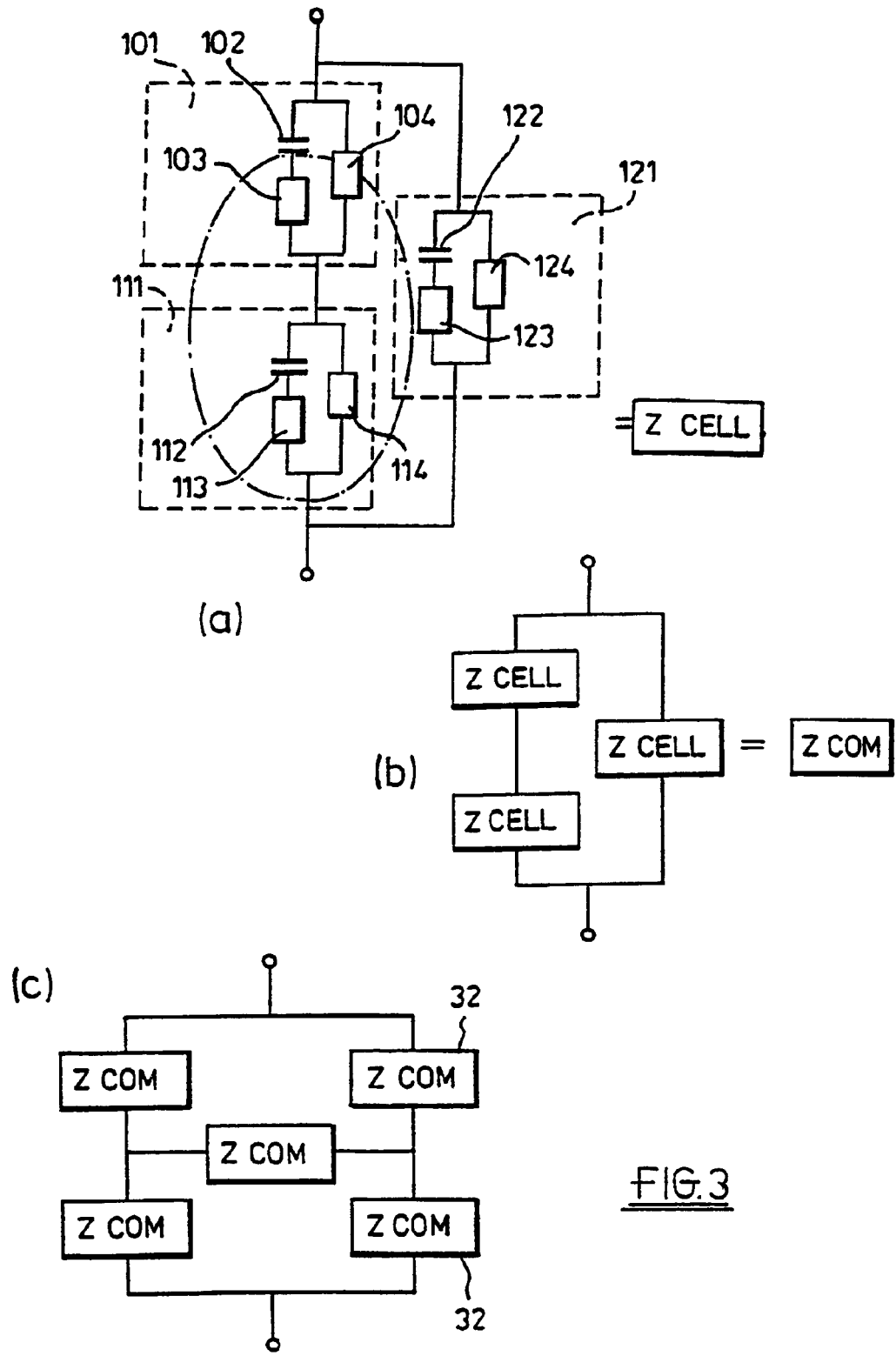
Figure 4:
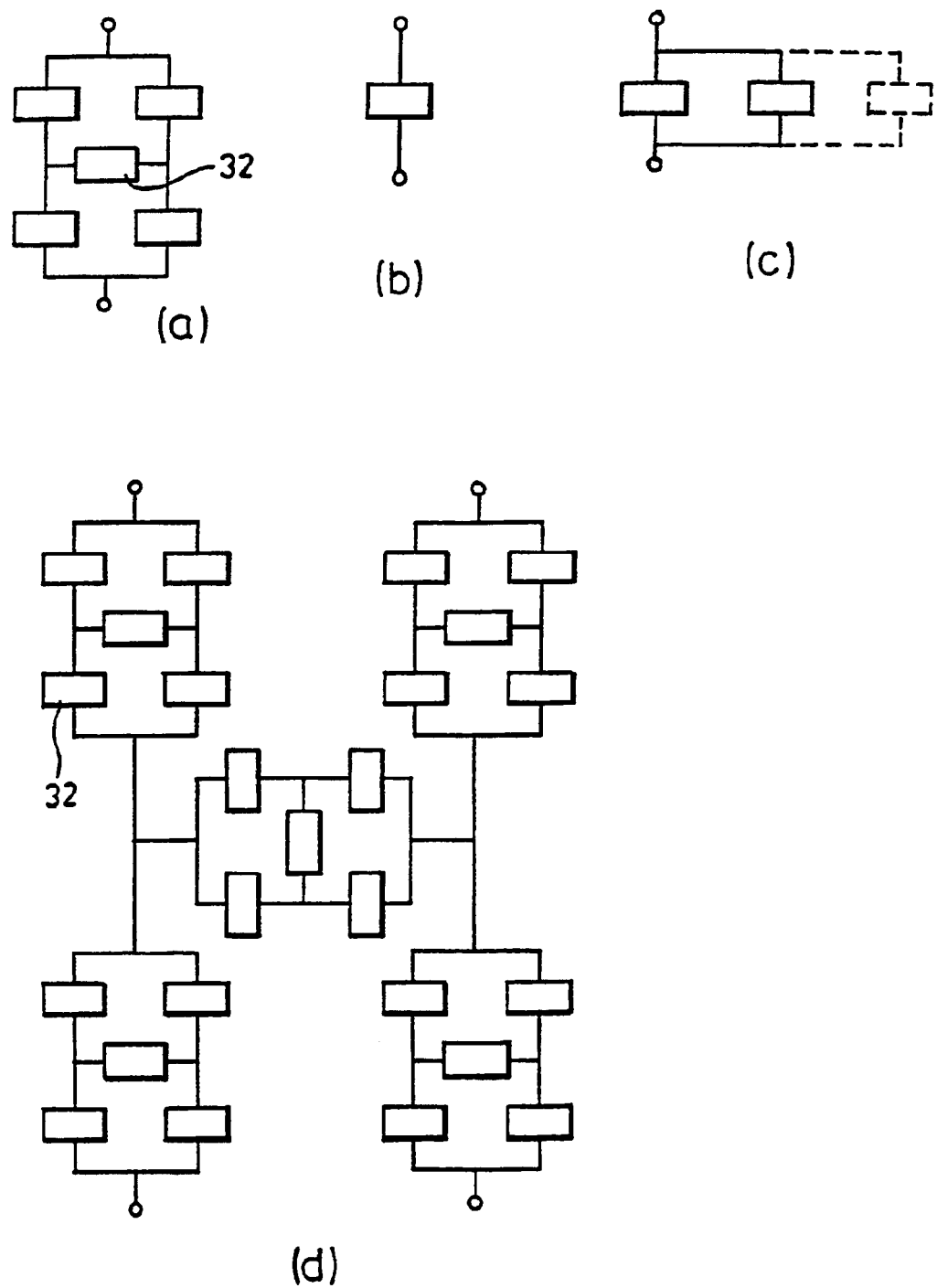

Methods and apparatus in accordance with the invention will now be described with reference to the accompanying drawings, in which:

FIG. 1   is a schematic diagram of an ETT apparatus;
FIG. 2   shows a cross sectional view of a female human breast;
FIG. 3   shows micro-level equivalent circuits - a) an equivalent circuit of a single cell, b) an equivalent circuit of a group of cells, c) an equivalent circuit of a number of groups of cells;
FIG. 4   shows a) an equivalent circuit of a number of groups of cells, b) the effective equivalent circuit for a number of groups of healthy cells, c) the effective equivalent circuit for a number of groups of diseased cells; and d) an equivalent circuit for a number of circuits of FIG. 4(a); and
FIG. 5   shows a micro-range model of a ductal system.

FIG. 1 shows EIT apparatus adapted to detect abnormalities in bodily matter 10 comprising:

electrical signal generating means 12 for generating electrical signals at a plurality of frequencies;

an electrode arrangement 14 for applying the electrical signals to the bodily matter 10, and detecting electrically impedance properties of the bodily matter 10; and data processing means 16, 18, 20 for correlating the detected electrical impedance properties with the presence or absence of abnormalities in the bodily matter 10;

in which electrical signals of a frequency greater than 1 MHz, preferably greater than 2 MHz, more preferably greater than 3 MHz and most preferably greater than 4 MHz are applied to the bodily matter.

At these high applied frequencies, differences between normal tissue and abnormal tissue are more pronounced, permitting the detection of abnormalities by EIT. It should be noted that the range of applied frequencies are certainly not restricted to this high frequency range. Indeed, it is preferably to utilise a wider bandwidth—in a representative example, frequencies in the range 1 kHz to 5 MHz are applied. Typically a number of spot frequencies across the desired bandwidth are applied, in sequential manner, to the bodily matter. However, it should be noted that the use of tine-to-frequency techniques is also within the scope of the invention. In this instance, an appropriate time varying waveform is applied to the electrode arrangement, and the response is monitored as a function of time. The time varying waveform can be considered to comprise electrical signals at a plurality of frequencies. The (time domain) response is then transformed into the frequency domain by an appropriate technique, such as a fast Fourier transform FFT).

In the present, non-limiting example, the electrical signal generating means 12 comprises a high impedance current source, converting the voltage output of a fully programmable Direct Digital Synthesis (DDS) 50 MHz microchip. An artificial upper limit of 5 MHz is placed on the output frequency, so that the waveform can be synthesised by the DDS chip in ten steps. Higher frequencies might be produced if desired—in principle, a 25 MHz "square" wave can be produced. Current is injected into the electrode arrangement 14, which is of the type well known in the tomographic field, comprising a set of current injection electrodes interlaced with voltage detection electrodes. A 2 dimensional thirty two electrode arrangement (comprising sixteen current injection electrodes and sixteen voltage detection electrodes) and a 1-dimensional four electrode arrangement have been used. The th two electrode system provides superior spatial resolution when the electrode systems are of identical dimensions. Detection of the voltage developed at the electrodes is performed using an EIT analogue hardware processing system 16. Data are then digitised by an analogue to digital convertor 18 and transferred to a computer 20 where the data can be stored and processed by a software system base upon commercially available products. The software system firstly collects the raw data from the electrodes and then a signal processing technique is applied to it to remove artefacts such as those caused by electrode-tissue contact problems, EIM system noise and system calibration. A filtered back-projection image method (Prof. David Barker, University of Sheffield) is then used to reconstruct an image. Image analysis is then performed to extract data from the reconstructed image, and the data is then correlated to that in a database conning data for normal and abnormal issues having been normalised for patient parameters including weight, age and body fat content, and the degree of correlation for the various tissue types determined in order to ascertain the probable nature of the tissue from the sections of the projected data. The software can retrieve data, convert the data to an impedance measure and reconstruct the data to produce a pixelated image.

Although the apparatus and method of the present invention might be used to dew many abnormalities, such as ulcers and thrombosis, a primary example is in the detection of carcinomas. As discussed previously, a particularly important example is the detection of breast carcinomas, more particularly early-stage breast carcinomas.

FIG. 2 shows sections through a human breast. Glandular tissue, shown generally at 22, is mainly located under the mammary papilla 24 and areola. The glandular tissue consists of a system of terminal ducts 26 which penetrate deep into the fibroadipose tissue of the breast. Each of the ducts is lined by columnar or cuboidal epithelium, comprising a continuous surface layer of epithehal cells with oval nuclei and an outer discontinuous layer of myoepithelial cells which have clear cytoplasm. The ducts 26 branch into ductules 28 and end in lobes 30. Additionally, there are regions of the breast in the lower and upper quadrants which consist of fat and muscle, and have no underlying glandular tissue. However, these regions are rarely host to any disease. In fact, cancer of the glandular tissue is the most common form of breast disease, of which infiltrating ductal carcinoma comprises 84% and infiltrating lobular carcinoma comprises 10% of all cases.

An important aspect of the present invention is the two-tier a or cascaded model of tissue impedance that is used to interpret the EIT measurements. FIG. 3a shows a RRC cascade equivalent circuit of a single cell, comprising a series and parallel arrangement of intra-cellular impedance $Z_i$ (111) comprising intra-cellular capacitance Ci (112), intracellular resistance Si (113) and intra-cellular cross-resistance Ri (114); extracellular impedance $Z_x$ (121) comprising extra-cellular fluid capacitance Cx (122), extra-cellular resistance Sx (123) and extra-cellular cross resistance Rx (124); and RRC membrane model $Z_m$ (101) comprising cell membrane capacitance Cm (102), membrane resistance Sm (103) and cross-membrane resistance Rm (104). If, as shown in FIG. 3a, this cellular equivalent circuit is denoted by the block "Zcell", then a group of cells can be represented by the circuit shown in FIG. 3b, and there may be multiple cascading levels of this circuit. In this circuit groups of individual cellular components Zcell are represented by a cascaded arrangement. The equivalent circuit of the combined cells shown in FIG. 3b is denoted by the block "Zcom". A still larger volume of tissue can be described by the equivalent circuit shown in FIG. 3c, in which the blocks "Zcom" are arranged in a different cascaded configuration to that shown in FIG. 3b. The process can be repeated to produce equivalent circuits for larger and larger cell groupings.

The fractal model of FIGS. 3a and 3b are applicable to breast tissue at a "micro" level scale (application to distances of up to about 100 μm), typically representing single cells, basic compound cells/tissue units, and compound tissues. At a "macro" level (applicable to distances in excess of about 100 μm) a different fractal model, namely that of FIGS. 3c and 4, is appropriate and is capable of representing compound tissues, integral single type cells and integral compound type cells. The exact distances at which the micro and macro models apply will differ slightly from tissue to tissue, and the exact cut-off point for a particular tissue may be readily determined by one skilled in the art. Where the "micro" and "macro" scale fractal models interact (i.e. at approximately 100 μm distances) the $Z_{com}$ units are the same. Thus a "micro" level fractal model $Z_{com}$ unit is used as a "macro" level fractal model $Z_{com}$ unit. This is referred to as the "ICI" model of integrated cell impedance. Thus, the overall model of tissue impedance is a fractal one, in the sense that the equivalent circuit at any give scale comprises sub-units in a common arrangement, and each of the sub-units itself comprises smaller sub-units which are also in the same common arrangement (i.e. the cascaded arrangement of FIGS. 3 and 4).

The fractal model of tissue impedance takes account of the physiological constitution of the cell/compound tissue/organ/system hierarchy. Furthermore, there is a direct rela tionship between the fractal model used and the resolution of the EIT sys employed—for example, at very high resolution the EIT technique might provide pixels of data which relate to relatively small groups of cells. This can be equated with the equivalent circuits of FIGS. 3b and 3c, which might be described as "micro-range" models of tissue impedance. At coarser resolution, the pixels comprising the tomographic image can be related to a "macro-range" model of tissue impedance in which compound tissues such as ductal and lobular structures are modelled, and can be aquated with the equivalent circuits of FIG. 4. Further sill, the fractal model is applicable at the high applied frequencies (i.e. the wide bandwiddth) utilised by the present invention. The fractal model can describe all stages of cancer development (0, 1, 2, 3, 4) in the ductal system and the lobular system.

Cancerous tissue gives rise to different electrical characteristics than those exhibited by normal, healthy tissue. Consider the equivalent circuit of the multi-cellular structure shown in FIG. 4a. In normal tissue, the potential across the central Zcom block 32 is around 0V. Under these conditions, the multi-cellular impedance can be represented by a single Zcom block, as shown in FIG. 4b. As a result, the number of dispersion (or corner) frequencies associated with the tissue will be constant, the ratio of intra and extra-cellular impedance (XIR) and the ratio of extra-cellular and membrane impedance (capacitance), XMR, will be constant.

In contrast, in diseased tissue there is a significantly non-zero potential across the central Zcom block. Under these circumstances, the electrical characteristics, for example dispersion characterstics, will be altered compared to normal tissue. In particular, the diseased tissue exhibits additional dispersions together with changes of XIR and XMR due to variations between the cascaded (parallel) Zcom blocks. Thus, detection of these additional dispersions, XIR and XMR (which might be overlaid) are indicative of the presence of diseased tissue and may be related to changes in the epithelium (degree of disruption of membrane base e.g. ductal/lobular system). FIG. 4c shows a representative equivalent circuit, although it should be noted that it may be appropriate to describe the tissue impedance with additional parallel components, such as that shown in broken lines in FIG. 4c. Tables 3 to 5 describe the correlation between detected electrical impedance properties and breast carcinoma pathology.

TABLE 3a

Matched Pathological/Electrical Parameters for Cancer Detection (in cellular range)

| Pathological properties of cancer cells | Electrical Properties of Cancer Cells (non-limiting) |
| --- | --- |
| 1. Dyskaryosis | Changes and/or large variations of intra-cellular impedance $Zi_{com}$ |
| 2. Abnormal nuclear-to-cytoplasmic ratio (NCR) | abnormal $Zi_{com}$, $Zx_{com}$, to $Zi_{com}$ ratio |
| 3. Abnormal inter-cellular cohesion | abnormal $Zx_{com}$ |
| 4. Abnormal membrane morphology | abnormal $Zm_{com}$, $Cm_{com}$, $Zx_{com}/Zm_{com}$, $Zx_{com}/Cm_{com}$, $Zm_{com}$, $Zi_{com}$ |

Notes:
Zi - intra-cellular impedance of single cell
$Zi_{com}$ - integral intra-cellular impedance among the cells
Zx - extra-cellular impedance of single cell
$Zx_{com}$ - integral extra-cellular impedance among the cells
Zm - membrane impedance of single cell
$Zm_{com}$ - integral membrane impedance among the cells
Cm - membrane capacitance of single cell
$Cm_{com}$ - integral membrane capacitance among the cells TABLE 3b Matched Pathological/Electrical Parameters for Cancer Detection (in compound tissue/compound cell range)

| Pathological properties of cancer cells | Electrical Properties of Cancer Cells (non-limiting) |
| --- | --- |

TABLE 4

Matched Pathological/Electrical parameters for Early Stage (non-infiltrate) Cancer Detection

| Pathological properties of early stage ductal/lobular cancers | Electrical Properties of the early stage ductal/lobular cancers |
| --- | --- |
| 1. changes and/or variation of intra-ductal/intra-lobular structures | changes of intra-ductal/intra-lobular impedance $Zi_{com}$ variation of $Zi_{com}$ (dependent on cancer types) |
| 2. changes and/or variation of extra-ductal/extra-lobular structures | changes extra-ductal/extra-lobular impedance $Zx_{com}$ |
| 3. changes and/or variation of "basement membrane" of ductal/lobular structure | changes "basement membrane" impedance $Zm_{com}$, $Cm_{com}$ (additional dispersion become evident) |
| 4. Abnormal morphalogy of extra-to-intra relationship of ductal/lobular structure | abnormal extra-to-intra ductal/lobular impedance ratio $Zx_{com}/Zi_{com}$; $Zx_{com}/Zm_{com}$; $Zx_{com}/Cm_{com}$ |

TABLE 5

Matched Pathological/Electrical parameters for Late Stages (Early-infiltrate and infiltrate stage) Cancer Detection

| Pathological properties of Late Stage cancers | Electrical Properties of the Late Stage ductal/lobular cancers |
| --- | --- |
| 1. changes and/or variation of intra-ductal/intra-lobular structures | changes of intra-ductal/intra-lobular impedance $Zi_{com}$ variation of $Zi_{com}$ (dependent on cancer types) |
| 2. changes and/or variation of extra-ductal/extra-lobular structures | changes extra-ductal/extra-lobular impedance $Zx_{com}$ |
| 3. penetration and/or larger variation of "basement membrane" of ductal/lobular structure | significantly change "basement membrane" impedance and capacitance $Zm_{com}$, $Cm_{com}$ (additional dispersions becoming significant) |
| 4. Abnormal morphology of extra-to-intra relationship of ductal/lobular structure | abnormal extra-to-intra ductal/lobular impedance ratio $Zx_{com}/Zi_{com}$; $Zx_{com}/Zm_{com}$; $Zx_{com}/Cm_{com}$ |

In intraductal or in-situ breast cancer, the malignant cells proliferate within the existing ductal system without destruction of the surrounding basement membrane. An example is lobular carcinoma in-situ (LCIS). LCIS is characterised by fig of the lobules with relatively small, uniform cells. Invasive lobular carcinoma has a tendency to spread diffusely between collagen fibres. FIG. 5 shows a micro-range model of a ductal system for the detection of early stage ductal carcinoma—a similar model describes lobular carcinoma. In FIG. 5, block 50 represents a RRC circuit for ductal basement (epithelial) wall membrane, block 52 represents a RRC circuit for intraductal (integral) impedance including the nucleus and block 54 represents a RRC circuit for extraductal impedance. Block 50 comprises membrane capacitance 56, membrane resistance 58 and cross membrane resistance 60. Block 52 comprises intraductal capacitance 62, intraductal resistance 64 and intraductal cross resistance 66. Block 54 comprises extraductal capacitance 68, extraductal resistance 70 and extraductal cross resistance 72.

In correlating the detected electrical impedance properties with the presence or absence of abnormalities such as carcinomas, it is advantageous to reference the detected impedance properties of the bodily matter to the detected electrical impedance properties of other bodily matter. This referencing procedure might comprise deriving a difference spectrum by subtracting "stantdard" responses from the measured responses. In the detection of breast carcinomas, it is useful to reference the impedance properties to the detected impedance properties of fatty tissue in the breast although the referencing might alternatively be with respect to normal gland tissue. A self referencing technique can be employed, in which high impedance fatty areas are masked from the image, followed by normalisation of the remaining data relative to a chosen frequency, such as 1 kHz.

In a different approach, higher order differentials (such as second order differentials) of change in impedance are analysed at low and high frequencies and can give useful information for e.g. tumorous tissues and the surrounding fatty and stroma tissues.

Numerous actors affect the measured impedance properties. An important factor is the temperature at which the measurement is made. This might be accounted for by building the temperate dependence into the correlation step, or preferably, by controlling the temperate at which the measurement is made. When in vitro measurements were performed on samples of tissue excised from a breast, it was found that the detected impedance properties vary depending on the orientation of the tissue, i.e. whether the current flow through the tissue is parallel or perpendicular to the excision. An additional factor was the fresh tissue handling procedure used-fresh blood-free issue ensured a reduction in the unexpected deviation between samples.

Another important factor in the detection of breast carcinomas is the age of the subject. Body size is also important. Both of these factors are linked with body fat and water content. It is possible to account for the variations by compiling a database of impedance properties corresponding to bodily matter of known composition, in particular consisting of measurements made from different subjects, having known breast fat content or, more practically, of known age. The database might comprise a library of such responses, or it might comprise an artificial intelligence system, such as a trained neural network.

In vitro measurements have been performed on a number of breast tissue samples supplied via a clinical collaboration with Glenfield General Hospital, Groby Road, Leicester, UK. Statistically significant differentiation was found between normal and stage 2 and stage 3 infiltrating ductal carcinomas. It has not proved possible to show significant in vitro differentiation between stage 1 or earlier cancers and normal tissuesat the present time. This has been due, as discussed above, to difficulties in the identification of such carcinomas conventionally, and therefore it is extremely difficult to obtain sufficient numbers of such samples in the first instance. It is believed that the present invention will be able to detect stage 1 or earlier-carcinomas, provided the spatial resolution of the interrogating EIT is commensurate with the small physical dimensions of these earlier stage tumours. This represents a major advantage over X-ray mammography.

It is highly desirable to perform in vivo detection since this is non-invasive. One way in which this might be performed in order to detect or screen for breast carcinomas is to dispose at least the electrode arrangement in a woman's brassiere. Such an arrangement can be made comfortable for the subject to wear. Furthermore, by disposing a plurality of electrode arrays in the brassiere, three dimensional images can be produced.

What is claimed is:

1. An electrical tomographic method for detecting abnormalities in bodily matter comprising the steps of:
    generating electrical signals having a frequency greater than 4 MHZ;
    applying the electrical signals to the bodily matter using an electrode arrangement;
    detecting electrical impedance properties of the bodily matter; and,
    using data processing means correlating the detected electrical impedance properties with the presence or absence of abnormalities in the bodily matter using a fractal model of tissue impedance.

2. The method according to claim 1, wherein the detected electrical impedance properties are selected from the group consisting of $Zi$, $Zx$, $Zx_{com}$, $Zm$, $Zm_{com}$, $Cm$ and $Cm_{com}$.

3. The method according to claim 1, wherein the data processing means correlates detected electrical impedance properties selected from the group consisting of $Zi_{com}$, $Zx_{com}$ to $Zi_{com}$ ratio, $Zx_{com}$, $Zm_{com}$, $Cm_{com}$, $Zx_{com}/ZM_{com}$, $Zxcom/Cm_{com}$, and $Zm_{com}$, $Zi_{com}$.

4. The method according to claim 1, wherein the data processing means correlates changes and/or large variations of intracellular impedance $Zi_{com}$ with the presence of dyskaryosis.

5. The method according to claim 1, wherein the data processing means correlates abnormal $Zx_{com}$, $Zx_{com}$ to $Zi_{com}$ ratio with abnormal nuclear-to-cytoplasmic ratio (NCR).

6. The method according to claim 1, wherein the data processing means correlates abnormal $Zx_{com}$ with abnormal inter-cellular cohesion.

7. The method according to claim 1, wherein the data processing means correlates abnormal $Zm_{com}$, $Cm_{com}$, $Zx_{com}/Zm_{com}$, $Zm_{com}/Cm_{com}$, $Zm_{com}$ $Zi_{com}$ with abnormal membrane morphology.

8. The method according to claim 1, wherein the data processing means correlates detected impedance properties selected from the group consisting of:
    i) $Zi_{com}$;
    ii) $Zx_{com}$;
    iii) $Zm_{com}$, $Cm_{com}$; and,
    iv) ratio $Zx_{com}/Zi_{com}$; $Zx_{com}/Zm_{com}$; $Zx_{com}/Cm_{com}$;
    with the presence of non-infiltrate, early-infiltrate or infiltrate stage cancer.

9. The method of claim 1, wherein the data processing means references the detected electrical impedance properties of the bodily matter to the detected electrical impedance of other bodily matter.

10. The method according to claim 9, being adapted to detect a breast carcinoma, wherein the detected impedance properties are of breast tissue and are referenced to detected electrical impedance properties of fatty tissue in the breast.

11. The method according to claim 1, wherein the data processing means is adapted to compare the detected electrical impedance properties with a database of impedance properties corresponding to bodily matter of known composition.

12. The method of claim 1, adapted to detect a carcinoma.

13. The method according to claim 1, adapted to detect a breast carcinoma.

14. The method according to claim 1, adapted to detect at least one of the group consisting of Stage 3, Stage 2 and Stage 1 carcinomas.

15. The method according to claim 1, wherein the electrode arrangement is disposed in a woman's brassiere.

16. The method according to claim 1, wherein the fractal model of tissue comprises a Zcom structure having a bridge configuration comprising first and second Zcom units in series with one another, third and fourth Zcom units in series with one another and in parallel with the first and second Zcom units, and a fifth Zcom unit bridging between the first, second, third and fourth Zcom units.

17. The method according to claim 16, wherein each Zcom unit further comprises at least one additional level of Zcom structure, each Zcom unit in the Zcom structure or the last of the Zcom structures comprising a Zcell structure comprising first, second and third Zcells, the first and second Zcells being in series, and the first and second Zcells being in parallel with the third Zcell, each Zcell optionally comprising at least one level of Zcell structure, each Zcell in the Zcell structure or the last of the Zcell structures comprising a single cell equivalent circuit comprising:

(i) a first membrane impedance circuit comprising cell membrane capacitance in series with membrane resistance, the cell membrane capacitance and membrane resistance being in parallel with cross-membrane resistance;

(ii) a second intracellular impedance circuit comprising intracellular capacitance in series with intracellular resistance, the intracellular capacitance and intracellular resistance being in parallel with intracellular cross-resistance; and (iii) a third extracellular impedance circuit comprising extracellular capacitance in series with extracellular resistance, the extracellular capacitance and extracellular resistance being in parallel with extracellular cross-resistance;

the first membrane impedance circuit and the second intracellular impedance circuit being in series, and the first membrane impedance circuit and the second intracellular impedance circuit being in parallel with the third extracellular impedance circuit.

18. An electrical tomographic method for detecting abnormalities in bodily matter comprising the steps of:

generating electrical signals at a plurality of frequencies;

using an electrode arrangement, applying the electrical signals to the bodily matter and detecting electrical impedance properties of the bodily matter; and using data processing means correlating the detected electrical impedance properties with a database of impedance properties corresponding to bodily matter of known composition in order to determine the presence or absence of abnormalities in the bodily matter;

wherein electrical signals of a frequency greater than 1 MHz are applied to the bodily matter; and characterised in that the data processing means correlates the detected electrical impedance properties with the presence or absence of abnormalities using a fractal model of tissue impedance which can be described as comprising a Zcom structure having a bridge configuration comprising first and second Zcom units in series with one another, third and fourth Zcom units in series with one another and in parallel with the first and second Zcom units, and a fifth Zcom unit bridging between the first, second, third and fourth Zcom units, each Zcom unit optionally comprising at least one additional level of Zcom structure, each Zcom unit in the Zcom structure or the last of the Zcom structures comprising a Zcell structure comprising first, second and third Zcells, the first and second Zcells being in series, and the first and second Zcells being in parallel with the third Zcell, each Zcell optionally comprising at least one level of Zcell structure, each Zcell in the Zcell structure or the last of the Zcell structures comprising a single cell equivalent circuit which can be described as comprising:

(i) a first membrane impedance circuit comprising cell membrane capacitance in series with membrane resistance, the cell membrane capacitance and membrane resistance being in parallel with cross membrane resistance;

(ii) a second intracellular impedance circuit comprising intracellular capacitance in series with intracellular resistance, the intracellular capacitance and intracellular resistance being in parallel with intracellular cross-resistance; and (iii) a third extracellular impedance circuit comprising extracellular capacitance in series with extracellular resistance, the extracellular capacitance and extracellular resistance being in parallel with extracellular cross-resistance;

the first membrane impedance circuit and the second intracellular impedance circuit being in series, and the first membrane impedance circuit and the second intracellular impedance circuit being in parallel with the third extracellular impedance circuit.

* * * * *

UNITED STATES PATENT AND TRADEMARK OFFICE
CERTIFICATE OF CORRECTION

PATENT NO. : 6,856,824 B1
DATED : February 15, 2005
INVENTOR(S) : Wei Wang et al.

It is certified that error appears in the above-identified patent and that said Letters Patent is hereby corrected as shown below:

Column 1,
Line 62, "mater" should be -- matter --.

Column 2,
Line 37, "fat" should be -- fatty --.
Line 43, "mater" should be -- matter --.
Line 56, "matte;" should be -- matter --.

Column 3,
Line 19, "body" should be -- bodily --.

Column 5,
Line 9, "tine-to-frequency" should be -- time-to-frequency --.
Line 17, "FFT)" should be -- (FFT) --.
Line 33, "th" should be -- thirty --.
Line 49, "conning" should be -- containing --.
Line 50, "issues" should be -- tissues --.
Line 58, "dew" should be -- detect --.

Column 6,
Line 14, "a" should be -- fractal --.

Column 7,
Line 11, "sill" should be -- still --.

UNITED STATES PATENT AND TRADEMARK OFFICE
CERTIFICATE OF CORRECTION

PATENT NO. : 6,856,824 B1
DATED : February 15, 2005
INVENTOR(S) : Wei Wang et al.

It is certified that error appears in the above-identified patent and that said Letters Patent is hereby corrected as shown below:

<u>Column 8,</u>
Line 51, "fig" should be -- filling --.

<u>Column 9,</u>
Line 5, " "stantdard"" should be -- "standard" --.
Line 19, "actors" should be -- factors --.

Signed and Sealed this

Seventh Day of March, 2006

JON W. DUDAS
*Director of the United States Patent and Trademark Office*